United States Patent
Mizusawa et al.

(10) Patent No.: US 10,655,059 B2
(45) Date of Patent: May 19, 2020

(54) COMPOUND AND CONTRAST AGENT FOR OPTICAL IMAGING HAVING THE COMPOUND

(71) Applicant: CANON KABUSHIKI KAISHA, Tokyo (JP)

(72) Inventors: Keigo Mizusawa, Tokyo (JP); Tatsuki Fukui, Yokohama (JP); Daisuke Sasaguri, Yokohama (JP); Atsushi Takahashi, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 157 days.

(21) Appl. No.: 15/533,971

(22) PCT Filed: Dec. 4, 2015

(86) PCT No.: PCT/JP2015/006045
§ 371 (c)(1),
(2) Date: Jun. 7, 2017

(87) PCT Pub. No.: WO2016/092799
PCT Pub. Date: Jun. 16, 2016

(65) Prior Publication Data
US 2017/0335182 A1    Nov. 23, 2017

(30) Foreign Application Priority Data

Dec. 9, 2014  (JP) ................. 2014-249439

(51) Int. Cl.
| | | |
|---|---|---|
| *C09K 11/06* | (2006.01) | |
| *C07D 209/60* | (2006.01) | |
| *G01N 33/49* | (2006.01) | |
| *A61K 49/00* | (2006.01) | |

(52) U.S. Cl.
CPC .......... *C09K 11/06* (2013.01); *A61K 49/0032* (2013.01); *A61K 49/0054* (2013.01); *C07D 209/60* (2013.01); *G01N 33/49* (2013.01); *A61K 49/001* (2013.01); *A61K 49/005* (2013.01); *A61K 49/0017* (2013.01); *C09K 2211/1466* (2013.01); *G01N 2800/7028* (2013.01)

(58) Field of Classification Search
None
See application file for complete search history.

(56) References Cited

U.S. PATENT DOCUMENTS

| | | |
|---|---|---|
| 2004/0141920 A1 | 7/2004 | Achilefu |
| 2009/0305410 A1 | 12/2009 | Mao |
| 2010/0311903 A1 | 12/2010 | Rajagopalan |
| 2011/0104070 A1 | 5/2011 | Kang |
| 2013/0230465 A1 | 9/2013 | Hermanson et al. |
| 2013/0230466 A1 | 9/2013 | Hermanson |
| 2014/0255312 A1 | 9/2014 | Hermanson |
| 2015/0157741 A1 | 6/2015 | Yamauchi |
| 2015/0165071 A1 | 6/2015 | Takahashi |

FOREIGN PATENT DOCUMENTS

| | | |
|---|---|---|
| JP | 2012-520856 A | 9/2012 |
| WO | 03/032901 A2 | 4/2003 |
| WO | 2009/078970 A1 | 6/2009 |

OTHER PUBLICATIONS

Ye, Y., et al, "Multivalent Carbocyanine Molecular Probes: Synthesis and Applications", Bioconjugate Chem, 2005, pp. 51-61, vol. 16, No. 1.

*Primary Examiner* — James W Rogers
(74) *Attorney, Agent, or Firm* — Canon U.S.A., Inc., IP Division

(57) ABSTRACT

To provide a compound having high T/B and a contrast agent for optical imaging. The compound has a molecular weight of a specific range, the compound in which two polyethylene glycols are bonded to a specific cyanine pigment through a linker. The present invention provides a compound which has a high T/B and which can be used as a contrast agent capable of imaging a tumor portion with high contrast.

11 Claims, 2 Drawing Sheets

COMPOUND AND CONTRAST AGENT FOR OPTICAL IMAGING HAVING THE COMPOUND

CROSS-REFERENCE TO RELATED APPLICATIONS

This application is a National Stage filing of International Application No. PCT/JP2015/006045 filed Dec. 4, 2015, which claims the benefit of Japanese Patent Application No. 2014-249439, filed Dec. 9, 2014, the disclosures of each of which are hereby incorporated by reference herein in their entirety.

TECHNICAL FIELD

The present invention relates to a compound and a contrast agent for optical imaging having the compound.

BACKGROUND ART

An optical imaging method is known as a method for noninvasively visualizing the information inside a living body. According to the optical imaging method, signals, such as acoustic waves and fluorescence, emitted from a substance (light-absorbing body) which absorbed light in an object to be measured when the object to be measured is irradiated with light are measured, and then imaged. By giving a pigment absorbing light in a near-infrared wavelength region, such as Indocyanine green (hereinafter sometimes abbreviated as ICG), into a living body, fluorescence or acoustic waves emitted from the pigment in the living body can also be measured. Therefore, pigments, such as ICG, can be used as a contrast agent for optical imaging.

Herein, in order to use a pigment as a contrast agent for tumors, it is suitable to bond a polymer to the pigment. Since the pigment generally has a low molecular weight, the pigment is promptly discharged from blood before accumulated in a tumor. However, by bonding a polymer, the pigment is hard to be discharged. Therefore, the pigment is accumulated in a tumor while circulating in blood, and, consequently, the accumulation amount in the tumor can be increased.

On the other hand, when the signal intensity from a portion other than a tumor site is lower than the signal intensity generated from the tumor site, a tumor portion can be visualized with high contrast. Therefore, it is desirable that the pigment does not remain for a long time in tissues other than the tumor portion, particularly blood vessels spreading in the entire living body. More specifically, it is desirable that a ratio (Tumor/Blood ratio, which is hereinafter sometimes abbreviated as T/B) of the accumulation amount in the tumor to the retention amount in blood of the contrast agent is high.

PCT Japanese Translation Patent Publication No. 2012-520856 (hereinafter referred to as PTL 1) describes a compound obtained by causing monoamine-PEG20k to react with Cy5 (Registered Trademark)-Bis NHS ester as an optical imaging agent. In the specification, k represents 1000 and, for example, 20 k is 20000. PEG20k herein means that the average molecular weight of PEG is 20000. In the specification, PEG is the abbreviation for polyethylene glycol. More specifically, a compound is disclosed in which the accumulation properties in tumor is increased by bonding two high molecular weight polymers (PEG) of 20 k to a pigment (Cy5 (Registered Trademark)).

CITATION LIST

Patent Literature

PTL 1: PCT Japanese Translation Patent Publication No. 2012-520856

SUMMARY OF INVENTION

As a result of an examination by the present inventors, it has been found that the T/B described above is low in a compound obtained by reaction of a monoamino PEG of 20 k with each of two ester groups of Cy5(Registered Trademark)-Bis NHS ester.

Thus, the present invention provides a compound which has a high T/B and which can be used as a contrast agent capable of imaging a tumor portion with high contrast.

Solution to Problem

A compound according to the present invention is a compound represented by any one of the following formulae (I) to (III) and having a molecular weight of 1600 or more and 40000 or less.

[Chem. 1]

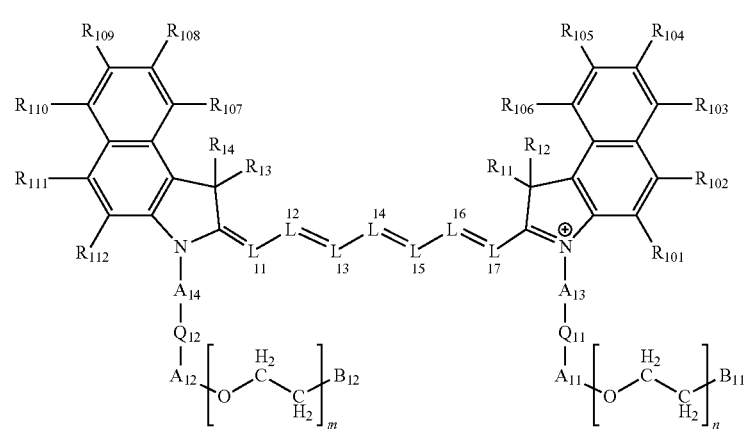

(I)

[Chem. 2]

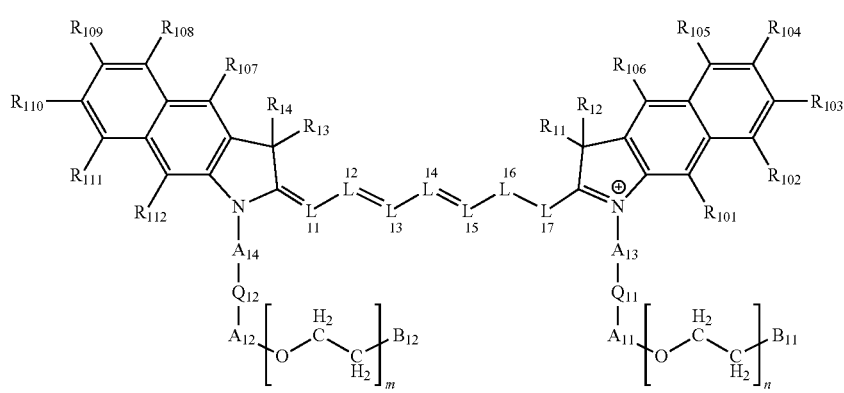

(II)

[Chem. 3]

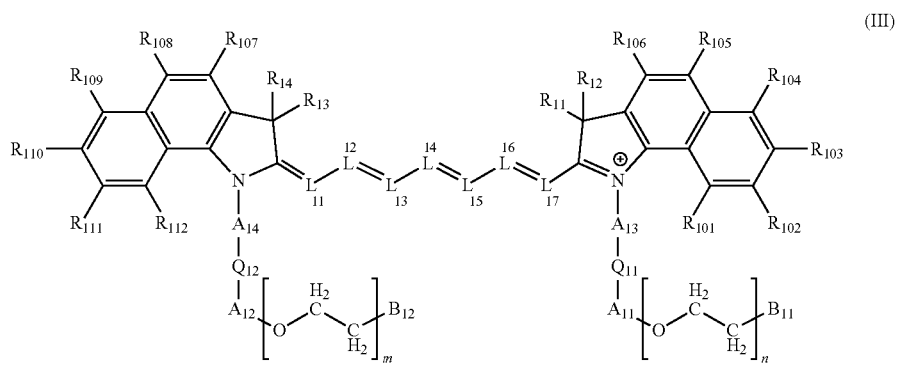

(III)

In Formulae (I) to (III) above, n and m each independently represent an integer of 1 or more, $R_{101}$ to $R_{112}$ each independently represent any one of a hydrogen atom, a halogen atom, an acetoxy group, an alkyl group having 1 to 18 carbon atoms, an alkyl ester group having 1 to 18 carbon atoms, and an alkylamide group having 1 to 18 carbon atoms, $R_{11}$ to $R_{14}$ each independently represent an alkyl group having 1 to 18 carbon atoms or a fluorinated alkyl group having 1 to 18 carbon atoms, $L_{11}$ to $L_{17}$ each independently represent substituted or unsubstituted methine and the substituent of methine is an alkyl group or a halogen atom having 1 to 4 carbon atoms, $L_{11}$ and $L_{13}$, $L_{12}$ and $L_{14}$, $L_{13}$ and $L_{15}$, and $L_{14}$ and $L_{16}$ may form a five-membered ring or a six-membered ring, $A_{11}$ to $A_{14}$ each independently represent an alkylene group having 1 to 9 carbon atoms or a fluorinated alkylene group having 1 to 9 carbon atoms, $Q_{11}$ and $Q_{12}$ each independently represent any one of —CONT-, —NTCO—, —NT(C=O)NT-, —NT(C=S)NT-, —NT(C=O)O—, —O—, —S—, —S(=O)$_2$NT-, —OP(=O)(OH)—, —S—S—, —CT=N—, —CT=N—NH—, —CT=N—NH—O—, and the following formulae (i) and (ii), represents any one of a hydrogen atom or an alkyl group having 1 to 5 carbon atoms, and $B_{11}$ and $B_{12}$ each independently represent any one of —H, —OCH$_3$, —NH$_2$, —CO$_2$H, —S(=O)$_2$OH, —P(=O)(OH)$_2$, and —OP(=O)(OH)$_2$.

[Chem. 4]

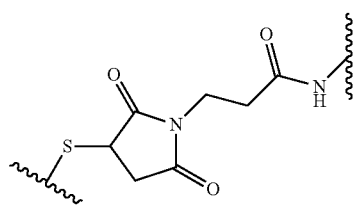

(i)

[Chem. 5]

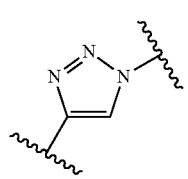

(ii)

Further features of the present invention will become apparent from the following description of exemplary embodiments with reference to the attached drawings.

DESCRIPTION OF EMBODIMENT

Figure 1:
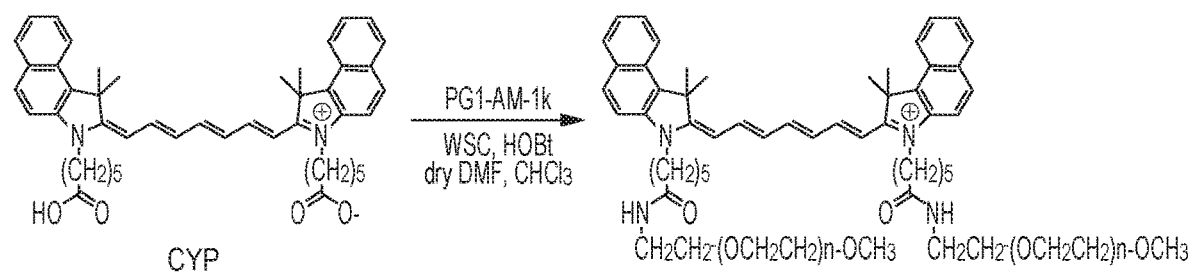
FIG. 1 is a view illustrating a synthesis process performed in Example 1 of the present invention.
Figure 2:
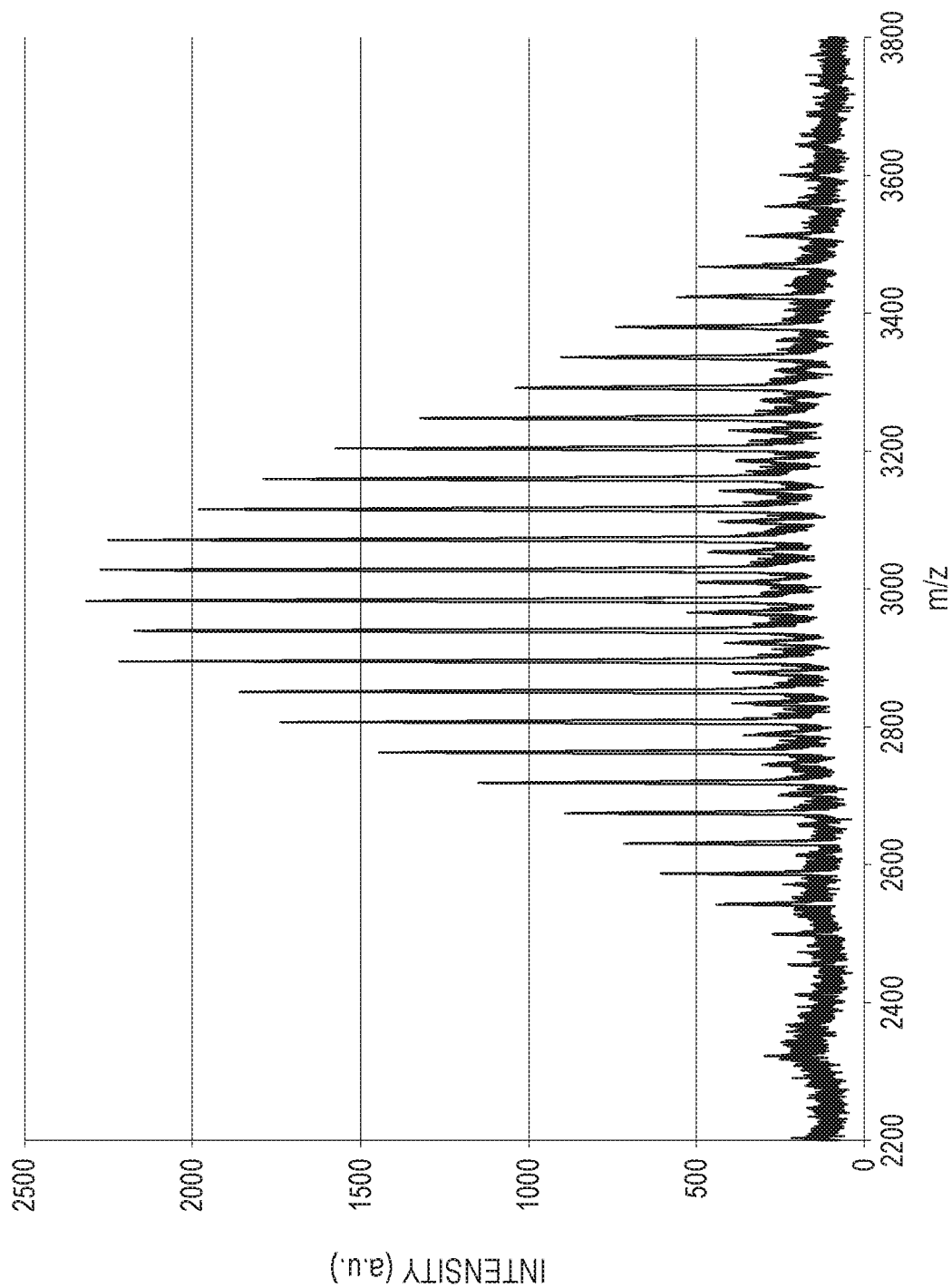
FIG. 2 is a view illustrating the Maldi-TOF-MS spectra of CYP-2PEG-1K×2 obtained by synthesis in Example 1 of the present invention.

Hereinafter, an embodiment of the present invention is described but the present invention is not limited thereto.

A compound according to this embodiment is a compound in which PEG having a relatively low molecular weight of 15 k or less, for example, is bonded to each nitrogen atom present in two indole rings of a cyanine pigment through a linker as shown in the following formulae (I) to (III). In such a compound in which a low molecule weight pigment is bonded to PEGs having a relatively low molecular weight, the molecular weight of the PEG is smaller than that of a former compound described in PTL 1, and therefore the retention properties in blood (B) is low but, as a result, the accumulation properties in tumor (T) is also low. On the other hand, the compound according to this embodiment has a naphthyl ring, and therefore the compound has one more rings as compared with the number of rings in the structure having a benzene ring, such as Cy5 (Registered Trademark) and Cy7 (Registered Trademark), and thus the hydrophobicity is high. Therefore, two or more of the compounds gather due to hydrophobic interaction to form an associate, so that the apparent molecular weight increases, and therefore the retention properties in blood is high. Moreover, it is considered that the state of being an associate is in a dynamic equilibrium state to a state of a compound alone, i.e., a reversible relationship. Therefore, while the compounds are accumulated in a tumor while forming an associate and remaining in blood, the compounds alone present in a fixed ratio are discharged.

Thus, in the compound according to this embodiment, the accumulation properties in tumor are high and the retention properties in blood are low and therefore the T/B is high.

The compound according to this embodiment is specifically a compound represented by any one of the following formulae (I) to (III) and having a molecular weight of 1600 or more and 40000 or less.

[Chem. 6]

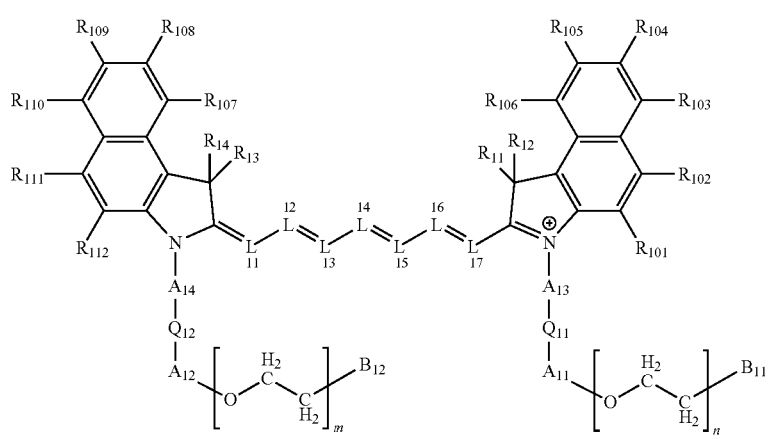

(I)

[Chem. 7]

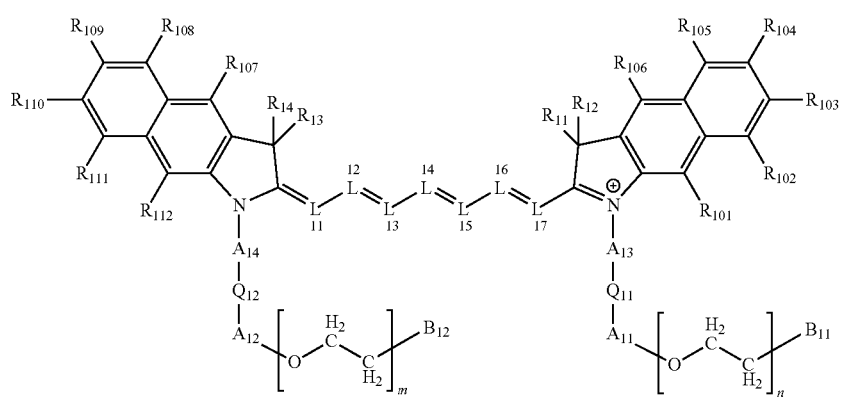

(II)

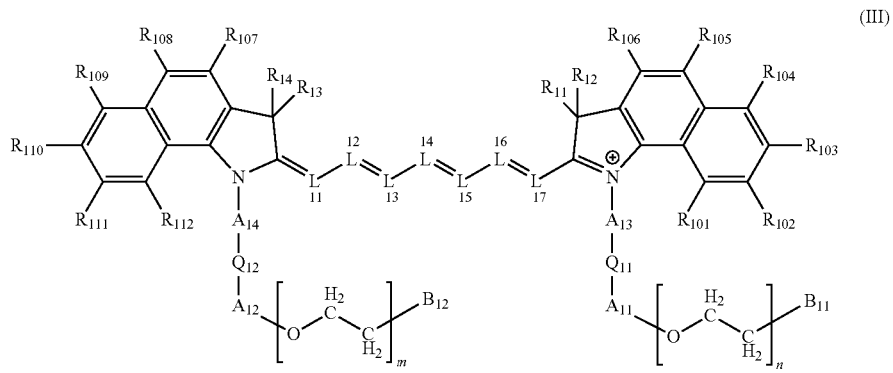

(III)

The molecular weight of the compound according to this embodiment is suitably 2000 or more and 25000 or less, more suitably 2500 or more and 11000 or less, and particularly suitably 2500 or more and 4500 or less from the viewpoint that the T/B is high. In Formulae (I) to (III), n and m each independently represent an integer of 1 or more. n and m each independently represent suitably an integer of 12 or more and 237 or less and more suitably an integer of 25 or more and 38 or less.

In Formulae (I) to (III) above, $R_{101}$ to $R_{112}$ each independently represent any one of a hydrogen atom, a halogen atom, an acetoxy group, an alkyl group having 1 to 18 carbon atoms, an alkyl ester group having 1 to 18 carbon atoms, and an alkylamide group having 1 to 18 carbon atoms. $R_{101}$ to $R_{112}$ are suitably hydrogen atoms.

In Formulae (I) to (III) above, $R_{11}$ to $R_{14}$ each independently represent an alkyl group having 1 to 18 carbon atoms or fluorinated alkyl group having 1 to 18 carbon atoms. In Formulae (I) to (III) above, $R_{11}$ to $R_{14}$ suitably represent methyl groups. In Formulae (I) to (III) above, $L_{11}$ to $L_{17}$ each independently represent substituted or unsubstituted methine and the substituent of methine is an alkyl group having 1 to 4 carbon atoms or a halogen atom. $L_{11}$ and $L_{13}$, $L_{12}$ and $L_{14}$, $L_{13}$ and $L_{15}$, and $L_{14}$ and $L_{16}$ may form a five-membered ring or a six-membered ring. $L_{11}$ to $L_{17}$ suitably represent unsubstituted methine. In this specification, a near-infrared wavelength band refers to a band of 600 nm or more and 1300 nm or less.

In Formulae (I) to (III) above $A_{11}$ to $A_{14}$ each independently represent an alkylene group having 1 to 9 carbon atoms or a fluorinated alkylene group having 1 to 9 carbon atoms. $A_{13}$ and $A_{14}$ each independently represent suitably an alkylene group having 1 to 9 carbon atoms, more suitably an alkylene group having 2 to 5 carbon atoms, and particularly suitably an alkylene group having 5 carbon atoms. $A_{11}$ and $A_{12}$ are suitably alkylene groups having 1 to 3 carbon atoms.

In Formulae (I) to (III) above, and $Q_{12}$ each independently represent any one of CONT-, —NTCO—, —NT(C=O)NT-, —NT(C=S)NT-, —NT(C=O)O—, —O—, —S—, —S(=O)$_2$NT-, —OP(=O)(OH)—, —S—S—, —CT=N—, —CT=N—NH—, —CT=N—O—, —CT=N—NH—O—, and the following formulae (i) and (ii). In $Q_{11}$ and $Q_{12}$, T represents any one of a hydrogen atom or an alkyl group having 1 to 5 carbon atoms. $Q_{11}$ and $Q_{12}$ suitably represent —CONH—.

[Chem. 9]

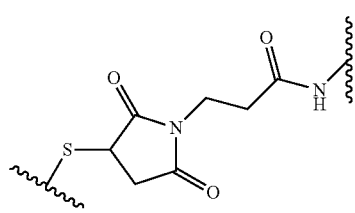

(i)

[Chem. 10]

(ii)

In Formulae (I) to (III) above, $B_{11}$ and $B_{12}$ each independently represent any one of —H, —OCH$_3$, —NH$_2$, —OH, —CO$_2$H, —S(=O)$_2$OH, —P(=O)(OH)$_2$ and —OP(=O)(OH)$_2$, $B_{11}$ and $B_{12}$ suitably represent —OCH$_2$.

In the compound according to this embodiment, Formula (I) above is suitably represented by the following formulae (I-1) and (I-2) and particularly suitably represented by the following formula (I-1).

[Chem. 11]

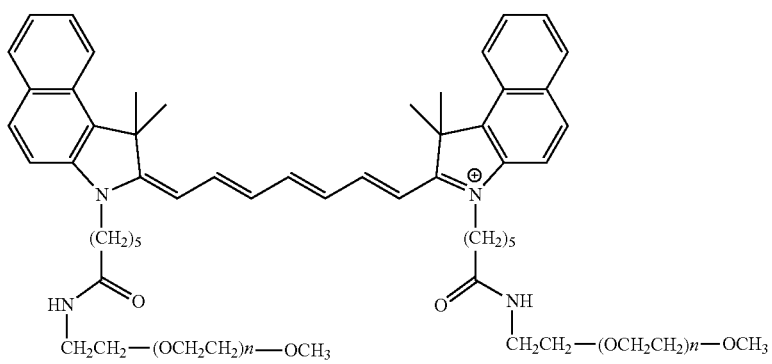

(I-1)

[Chem. 12]

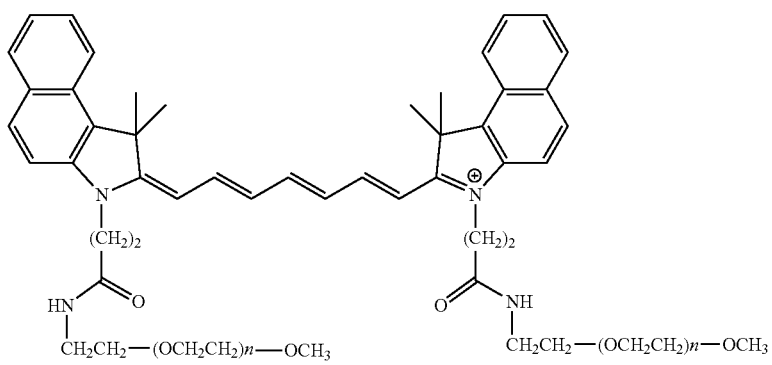

(I-2)

In Formulae (I-1) and (I-2) above, n is an integer of 1 or more.

Method for Producing Compound According to this Embodiment

A method for producing the compound according to this embodiment is described.

Synthesis of Compound

The compound in this embodiment is prepared by bonding PEG and a specific cyanine compound by a coupling reaction through a functional group of each of the PEG and the specific cyanine compound. For example, the PEG is bonded through a substituent of a nitrogen atom present in the indole ring of the specific cyanine compound. It is suitable to cause amide bonding through an amino group of PEG having an amino group and a carboxyl group of a specific cyanine compound.

The PEG and the specific cyanine compound may be bonded through an amide bond, a urea bond, a thiourea bond, a urethane bond, an ether bond, a thioether bond, a sulfonamide bond, a phosphate ester bond, a disulfide bond, an imine bond, a hydrazone bond, a thioether bond by thiol addition to a maleimide group, or a triazole bond as a linking group of the cyanine compound and the PEG.

Herein, the amide bond, the urea bond, the thiourea bond, the urethane bond, the ether bond, the thioether bond, the sulfonamide bond, and the triazole bond are relatively stable bonds in a living body. Since the thioether bond by thiol addition to a maleimide group, the imine bond, and the hydrazone bond can be formed without using a condensing agent and the like, a load of removing the condensing agent in a purification process can be reduced.

The specific cyanine pigment bonded to the PEG can be purified by known purification methods, such as an ultrafiltration method, size exclusion column chromatography, and a silica gel column chromatography method. The bond of the PEG and the specific cyanine compound may be direct bond through functional groups, such as an amino group, of the PEG described above and the substituent of the specific cyanine compound or may be bond through various crosslinking materials (crosslinkers).

As a method for causing the specific cyanine pigment and the PEG to react with each other, any one of a method employing a condensing agent as a reaction of a carboxyl group and an amino group, a method including forming a salt, and then performing condensation by a dehydration reaction, a method employing a dehydrating agent, and a method including converting a carboxyl group to acyl chloride or succinimide ester, and then causing the converted substance to react with an amino group can be used.

As the condensing agent, a carbodiimide-based condensing agent, an imidazole-based condensing agent, a triazine-based condensing agent, a uranium-based condensing agent, a phosphonium-based condensing agent, and the like can be used.

As an example of the carbodiimide condensing agent, N,N'-dicyclohexylcarbodiimide (DCC), N,N'-diisopropylcarbodiimide (DIC), and water-soluble carbodiimide (WSC) can be mentioned. It is suitable to use 1-hydroxybenzotriazole (HOBt) and 1-hydroxyazabenzotriazole (HOAt) as a reaction accelerator in combination. This is because the reaction time can be reduced by the use of the condensing agent and the reaction accelerator in combination and also a larger number of the compounds in this embodiment can be produced.

The use amount of the condensing agent is suitably in the range of 2.0 times or more by mole based on the use amount of the specific cyanine compound. This is because a larger number of the compounds in this embodiment in which two PEGs are bonded to one specific cyanine compound can be produced. Moreover, the condensing agent itself can also be used as a reaction solvent.

The use amount of the PEG to be used when synthesizing the compound according to this embodiment is suitably 2.0 times or more by mole based on the use amount of the specific cyanine compound. This is because, when the use amount of the PEG is larger, the remaining amount of the compound in which only one PEG is bonded to one specific cyanine compound can be reduced, and therefore a load of removing an unreacted compound in a purification process is low.

An organic solvent to be used in the reaction process in this embodiment is not particularly limited insofar as the specific cyanine compound and the PEG can be bonded to each other. Examples of the organic solvent to be used in the reaction process include hydrocarbons, such as hexane, cyclohexane, and heptane, ketones, such as acetone and methyl ethyl ketone, ethers, such as dimethylether, diethylether, and tetrahydrofuran, halogenated hydrocarbons, such as dichloromethane, chloroform, carbon tetrachloride, dichloroethane, and trichloroethane, aromatic hydrocarbons, such as benzene and toluene, aprotic polar solvents, such as N,N-dimethyl formamide (hereinafter sometimes abbreviated as DMF) and dimethylsulfoxide (DMSO), and pyridine derivatives. Two or more kinds of the organic solvents can be mixed for use.

Suitably, aprotic polar solvents, such as DMF and dimethylsulfoxide, and halogenated hydrocarbons, such as dichloromethane and chloroform, are mentioned. This is because the specific cyanine compound and the PEG have high solubility in the organic solvents, and thus the reaction can be performed in a state where the compound is sufficiently dispersed. The use amount of the organic solvent to be used when producing the compound can be determined as appropriate according to the reaction conditions and the like. The reaction temperature when performing the synthesis for obtaining the compound according to this embodiment is not particularly limited and is usually 0° C. or more and is equal to or less than the boiling point of the solvent. However, it is suitable to perform the reaction at the optimal temperature for the condensing agent to be used. The reaction time is in the range of 1 hour to 120 hours, for example.

Purification of Compound

For the purification of the compound in this embodiment, a technique is not particularly limited insofar as a bonded body of a specific cyanine pigment and a compound having PEG, and then an unreacted compound can be removed.

Examples of methods for isolating and purifying the compound according to this embodiment include reverse phase chromatography using high-polarity solvents, such as water, acetonitrile, and methanol, normal phase chromatography using organic solvents, gel filtration chromatography, ultrafiltration, dialysis, reprecipitation, and re-crystallization, and the like. Examples of the organic solvents to be used in the purification include hydrocarbons, such as hexane, cyclohexane, and heptane, ketones, such as acetone and methyl ethyl ketone, ethers, such as dimethyl ether, diethylether, and tetrahydrofuran, halogenated hydrocarbons, such as dichloromethane, chloroform, carbon tetrachloride, dichloroethane, and trichloroethane, aromatic hydrocarbons, such as benzene and toluene, aprotic polar solvents, such as N,N-dimethyl formamide and dismethyl sulfoxide, alcohols, such as a pyridine derivative, methanol, and ethanol. Two or more kinds of these solvents can be mixed for use. Suitably, halogenated hydrocarbons, such as dichloromethane and chloroform, and alcohols, such as methanol and ethanol, are mentioned. This is because, when these solvents are used, the solubility of the cyanine pigment and the bonded body is improved. As a result, the purification can be performed in a state where the specific cyanine pigment and the compound according to this embodiment are sufficiently dispersed. A method for drying the compound according to this embodiment is not particularly limited. Examples of the drying method include methods using a usual evaporator, a vacuum dryer, a freeze dryer, and the like.

PEG

The PEG is a water-soluble polymer and demonstrates effects, such as an increase in serum half-life and a reduction in immunogenicity of protein.

The molecular weight of the PEG to be used for preparing the compound according to this embodiment is suitably 15000 or less, more suitably 5000 or less, and particularly suitably 2000 or less.

In PEG having a relatively low molecular weight of 20000 or less, the retention properties in blood are low.

When the molecular weight of the PEG is smaller, the molecule size becomes smaller in three dimension, and therefore steric repulsion does not occur and an aggregation effect improves.

It is considered that, when the molecular weight of the PEG is several hundreds, the hydrophobicity of one molecule becomes high as a whole, which causes enlargement of an associate or nonspecific adsorption to tumor cells and normal cells, so that the accumulation amount in tumor decreases.

Therefore, it is most suitable to use PEG having a molecular weight of 1000 to 2000.

The "molecular weight" of the PEG or the compound according to this embodiment described in this specification refers to a weight average molecular weight (Mw) of a molecular weight distribution obtained from mass spectrometry by Maldi-TOF-MS.

The PEG in this embodiment is one having at least one or more reactive functional groups which can be covalently bonded to the specific cyanine compound in one PEG molecule, strictly a PEG derivative. Herein, the reactive functional group can be selected as appropriate according to a functional group of a pigment to be bonded. The reactive functional group is suitably an amino group, a hydroxyl group, a thiol group, a carbonyl group, a sulfhydryl group, an epoxy group, a glycidyl group, an N-succinimidyloxycarbonyl group, a sulfosuccinimidyloxycarbonyl group, an N-maleimide alkylene group, and the like, for example.

Examples of functional groups at the terminal of the PEG of the compound according to this embodiment include —H, —OCH$_3$, —NH$_2$, —OH, —CO$_2$H, —S(=O)$_2$OH, —P(=O)(OH)$_2$, and —OP(=O)(OH)$_2$. Since these functional groups are hydrophilic, the aggregation properties of a hydrophobic portion of the compound according to this embodiment can be increased. In this embodiment, a compound represented by the following formula (p1) is suitably used as the PEG derivative.

[Chem. 13]

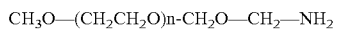
 (p1)

In Formula (I-1) above, n is an integer of 1 or more.

One in which Mw of Formula (p1) is 1000 is PG1-AM-1k (manufactured by Nanocs Inc), one in which Mw is 550 is PG1-AM-550 (manufactured by Nanocs Inc.), one in which Mw is 2000 is PG1-AM-2k (manufactured by Nanocs Inc.), one in which Mw is 5000 is PG1-AM-5k (manufactured by Nanocs Inc.), one in which Mw is 10000 is PG1-AM-10k (manufactured by Nanocs Inc.), and one in which Mw is 20000 is PG1-AM-20k (manufactured by Nanocs Inc.).

In this embodiment, as the PEG derivative, SUNBRIGHT (Registered Trademark) PA Series (manufactured by NOF CORPORATION.), such as SUNBRIGHT MEPA-20H, SUNBRIGHT MEPA-50H, SUNBRIGHT MEPA-12T, SUNBRIGHT MEPA-20T, SUNBRIGHT MEPA-30T, and SUNBRIGHT MEPA.-40T, SUNBRIGHT (Registered Trademark) EA Series (manufactured by NOF CORPORATION.) (Compound represented by Formula (p1) above), such as SUNBRIGHT ME-050EA, SUNBRIGHT ME-100EA, SUNBRIGHT ME-200EA, SUNBRIGHTME-300EA and SUNI3RIGHT ME-400EA, mPEG-Amine (MW 550, 1000, 2000, 3400, 5000, 10000, 20000) (manufactured by Laysan Bio), and the like can be used.

Specific Cyanine Compound

In this embodiment, the structure of the cyanine compound may have a hydrophobic group in the indole ring and the polymethine chain of the cyanine pigment. This is because the introduction of a halogen atom, an acetoxy group, an alkyl group, an alkyl ester group, and an alkylamide group can increase the hydrophobicity of the pigment and can increase the aggregation properties as compared with an unsubstituted cyanine compound. When the number of the carbon atoms of the alkyl chains is larger, the hydrophobicity and the aggregation properties further increase. In this embodiment, the aromatic ring site of the cyanine compound may be a benzo[e]indole represented by Formula (I) above, benzo[f]indole represented by Formula (II) above, and benzo[g]indole represented by Formula (III) above. This is because the hydrophobicity and the aggregation properties of these isomers are almost equal to each other.

The polymethine chain of the cyanine compound may be unsubstituted or substituted by an alkylene chain, a cyclopentyl ring, or a cyclohexyl ring. This is because the introduction of the substituents can increase the hydrophobicity of the pigment site and can increase the aggregation properties without changing the conjugate structure of the cyanine compound.

As the specific cyanine pigment according to this embodiment, C5cypate (hereinafter sometimes abbreviated as CYP) represented by the following formula (d1) and cypate (hereinafter sometimes abbreviated as C2CYP hereinafter) represented by the following formula (d2) are suitably used and the C5cypate is more suitably used.

[Chem. 14]

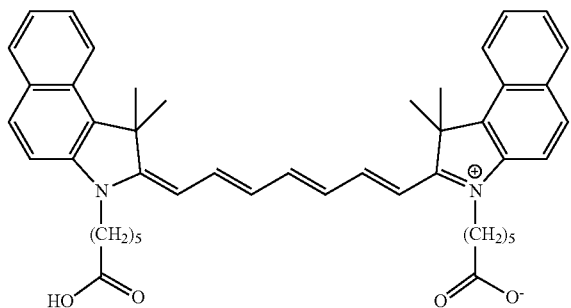

(d1)

[Chem. 15]

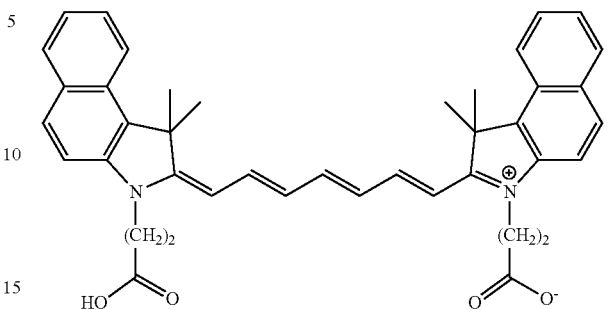

(d2)

Linker Portion

The linker portion of the bonded body of the cyanine compound and the PEG is suitably an alkylene chain or a fluorinated alkylene chain. The alkylene chain is suitably an alkylene chain in which the number of carbon atoms is 1 or more and 9 or less and the number of carbon atoms is more suitably 2 or more and 5 or less. As an increase in the number of carbon atoms, the hydrophobicity is higher and the aggregation effect can be increased.

A fluorinated alkylene chain in which the number of carbon atoms is 6 or less is stable and has high safety and high hydrophobicity, and therefore the aggregation effect of the compound according to this embodiment can be increased.

Use of Compound According to this Embodiment

Contrast Media for Optical Imaging

A contrast agent for optical imaging according to this embodiment has the compound according to this embodiment and a dispersion medium. Herein, the dispersion medium is a liquid substance for dispersing the compound according to this embodiment. For example, physiological saline, distilled water for injection, phosphate buffered saline, Ringer's solution, a glucose solution, and the like are mentioned. In the contrast agent for optical imaging according to this embodiment, the compound according to this embodiment may be dispersed beforehand in the dispersion medium or the compound according to this embodiment and the dispersion medium are formed into a kit, and then the compound may be dispersed in the dispersion medium for use before given into a living body. The contrast agent for optical imaging according to this embodiment may further have pharmacologically acceptable additives, such as a diluent, in addition to the compound or the dispersion medium, e.g., a vasodilator, a pH adjuster, an isotonizing agent, a stabilizer, a solubilizing agent, and the like. The contrast agent for optical imaging according to this embodiment may further contain additives to be used in freeze-drying. As an example of the additives, glucose, lactose, mannitol, polyethylene glycol, glycine, sodium chloride, and sodium hydrogen-phosphate are mentioned. The additives may be used alone or in combination of two or more kinds thereof.

With respect to the contrast agent for optical imaging according to this embodiment, the pH of the contrast agent solution is adjusted to 5.0 or more and 8.0 or less and more suitably 7.0 or more and 7.4 or less when given into a living body. When the contrast agent contains a physiological salt solution, the osmotic pressure ratio of the contrast agent solution to the physiological salt solution is suitably 0.01 to 2.0 and more suitably 1.0.

In this embodiment, the optical imaging means performing imaging by emitting light. By irradiating the contrast agent according to this embodiment with light, photoacoustic imaging can be carried out by detecting emitted acoustic waves and fluorescent imaging can be carried out by detecting emitted fluorescence. The photoacoustic imaging is a concept including photoacoustic tomography (tomography imaging). When the contrast agent for optical imaging according to this embodiment is used for the fluorescent imaging, the contrast agent is referred to as a contrast agent for fluorescent imaging. When used for the photoacoustic imaging, the contrast agent is referred to as a contrast agent for photoacoustic imaging.

Imaging of Tumor

When the contrast agent for optical imaging according to this embodiment is given into a living body, the contrast agent is accumulated in a tumor site and also the remaining amount of the contrast agent in blood is low. As a result, when the contrast agent for optical imaging according to this embodiment is given into a living body, and then acoustic waves and fluorescence emitted from the living body by irradiating the living body with light are detected, the acoustic waves and the fluorescence emitted from a tumor site can be made larger than acoustic waves and fluorescence emitted from a normal portion.

The accumulation amount in tumor/the retention amount in blood (T/B) of the contrast agent for optical imaging according to this embodiment is suitably larger than 1.2 and more suitably 1.5 or more. The tumor site can be imaged with higher contrast as an increase in the T/B ratio.

Imaging of Lymph Node

The contrast agent for optical imaging according to this embodiment can also be used for imaging of a lymph node besides the tumor imaging. The contrast agent for optical imaging according to this embodiment is particularly suitably used for a contrast agent for a sentinel lymph node. This is because the compound according to this embodiment has a size larger than the size of a pigment alone, and therefore it is expected that a larger amount of the compound is accumulated in the sentinel lymph node and the accumulation properties are improved.

Photodynamic Therapy

The compound according to this embodiment is caused to generate active oxygen species by light irradiation and can also be used for medical treatment of tumors by a photodynamic, therapy. This is because the remaining amount in blood vessels of the compound according to this embodiment is small, and therefore only tumor cells can be damaged without the active oxygen species generated from the compound according to this embodiment by light irradiation damaging blood vessels around the tumor.

Capturing Molecule

A capturing molecule may be further bonded to the compound according to this embodiment. The capturing molecule in this embodiment refers to a substance which is specifically bonded to a target site, such as a tumor, a substance which is specifically bonded to a substance present around a target site, and the like and can be arbitrarily selected from chemical substances, such as biomolecules and pharmaceutical agents. Specifically, artificial antibodies, such as antibodies, antibody fragments, and single chain antibodies, enzymes, bioactive peptides, glycopeptides, sugar chains, lipids, molecule recognizing compounds, and the like are mentioned. These substances can also be used alone or in combination of two or more kinds thereof. By the use of the compound according to this embodiment to which the capturing molecule is chemically bonded, a target site can be specifically detected and the dynamic state, localization, medicinal effects, metabolism, and the like of a target substance can be traced.

Imaging Method Using Contrast Agent According to this Embodiment

Optical Imaging Method

A method for detecting the compound according to this embodiment given into a living body using a photoacoustic imaging device or a fluorescent imaging device is described. The method for detecting the compound according to this embodiment has the following processes (a) and (b). However, the photoacoustic imaging method or the fluorescent imaging method according to this embodiment may include processes other than the processes described below:

(a) Process of irradiating a sample to which the compound according to this embodiment was given with light in a wavelength region of 600 nm to 1300 nm; and
(b) Process of detecting acoustic waves and fluorescence generated from the compound present in the sample.

The method may have a process of reconstructing a spatial photoacoustic signal intensity distribution or fluorescence signal intensity distribution from the wavelength, the phase, the time information, and the like of the acoustic waves or the fluorescence obtained in (b) above. The three-dimensional image reconstruction can be performed based on the wavelength, the phase, and the time information of the photoacoustic signals or the fluorescence obtained in the process (b). The data obtained by the image reconstruction may have any form insofar as the position information of the intensity distribution of the photoacoustic signals or the fluorescence can be grasped. For example, data representing the photoacoustic signal intensity or the fluorescence intensity on three-dimensional space may be acceptable or data representing the photoacoustic signal intensity or the fluorescence intensity on a two-dimensional plane may be acceptable. It is also possible to acquire information on the same observation target by different imaging methods, and then acquire the positional correspondence relationship between the acquired information and the intensity distribution of the photoacoustic signals or the fluorescence.

In the process (a) above, a sample to which the compound according to this embodiment is given by methods, such as oral administration or injection, can be used.

In the process (b) above, a device generating light to be emitted to a sample and a device detecting photoacoustic signals or fluorescence emitted from the compound according to this embodiment are not particularly limited.

A light source irradiating a sample with light in the process (b) above is not limited insofar as laser pulse light of at least one wavelength selected from the range of 600 nm to 1300 nm can be emitted to the sample. Examples of the device emitting the laser pulse light include a titanium sapphire laser (LT-2211-PC, manufactured by Lotis TII), an OPO laser (LT-2214 OPO, manufactured by Lotis TII), and an alexandrite laser, for example.

The device detecting acoustic waves is not particularly limited and various devices can be used. For example, the detection can be carried out using a commercially available photoacoustic imaging device (Nexus128, manufactured by Endra Inc.).

The device detecting fluorescence is not particularly limited and various devices can be used. For example, the detection can be carried out using a commercially available fluorescence imaging device (IVIS Imaging System, manufactured by PerkinElmer Inc.).

The imaging method employing the compound according to this embodiment can image a target site, such as a tumor, a lymph node, or a blood vessel, by passing through the processes (a) and (b) above.

EXAMPLES

Hereinafter, the present invention is described in more detail with reference to Examples but the present invention is not limited to Examples. Materials, composition conditions, reaction conditions, and the like can be freely altered insofar as a contrast agent having the same functions and effects can be obtained. In the following description, Mw represents the molecular weight.

The structures of samples prepared in this example, CYP-2PEG-0.35K×2, CYP-2PEG-0.55K×2, CYP-2PEG-1K×2, CYP-2PEG-2K×2, CYP-2PEG-5K>2, CYP-2PEG-10K×2, and CYP-2PEG-20K×2 are all represented by Formula (I-1) above. The samples mentioned above are different in the molecular weight. "CYP-2PEG-0.35K×2" means that the molecular weight of one PEG portion of two PEG portions ($OCH_2CH_2$) of Formula (I-1) is 0.35 k. The same applies to the other samples.

The typical structure of C2CYP-2PEG-1K×2 is represented by Formula (I-2) above. The typical structure of C10CYP-2PEG-0.35K×2 is represented by the following formula ((1:1). The samples mentioned above are different in the molecular weight. "C2CYP-2PEG-1K×2" means that the molecular weight of one PEG portion of two PEG portions ($OCH_2CH_2$) of Formula (I-2) is 1 k. The same applies to the other samples.

[Chem. 16]

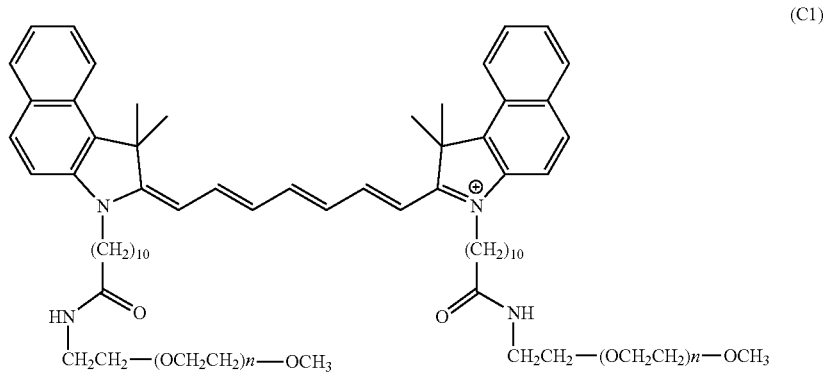

(C1)

The typical structures of cy7-2PEG-20K×2 and cy7-2PEG-1K×2 are represented by the following formula (C2). The typical structures of cy5-2PEG-20K×2 and cy5-2PEG-1K×2 are represented by the following formula (C3). The samples mentioned above are different in the molecular weight. "cy7-2PEG-20K×2" means that the molecular weight of one PEG portion of two PEG portions ($OCH_2CH_2$) of the following formula (C2) is 20 k. The same applies to the other samples.)

[Chem. 17]

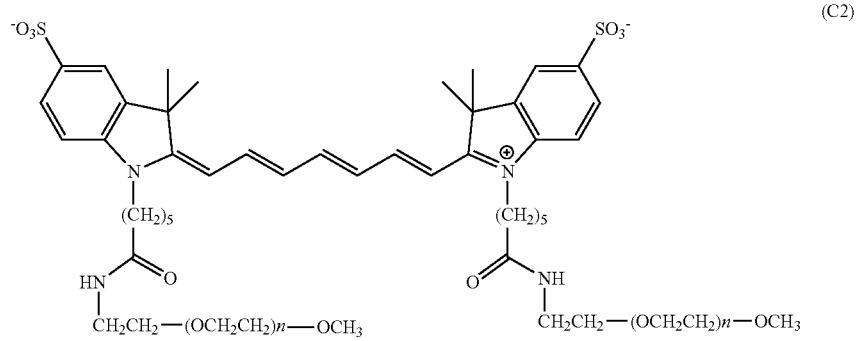

(C2)

-continued

[Chem. 18]

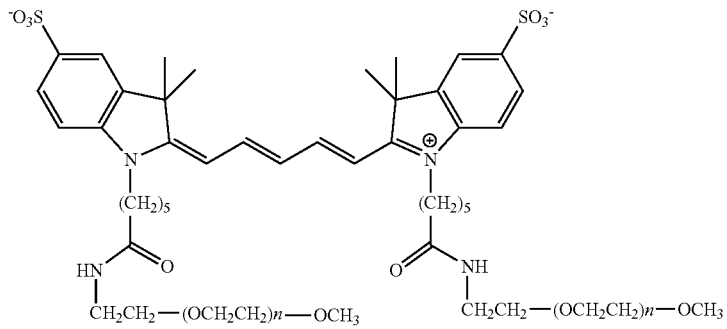

(C3)

Analysis Method

The structure of each compound obtained in each following examples was determined using ¹H-NMR (Bruker Avance 500, manufactured by Bruker, Resonance frequency: 500 MHz) measuring device.

For the absorption spectrum measurement performed in the following examples, an ultraviolet and visible light absorption spectrum measuring device (manufactured by PERKIN ELMER, Lambda Bio 40) was used.

For the mass spectrometry (MS) performed in the following examples, MALDI-TOF-MS (manufactured by Bruker Daltonics K.K., Autoflex) was used.

For the mass spectrometry performed in the following comparative example 2, a gel permeation chromatograph analyzer (manufactured by Showa Denko K.K., Shodex GPC-101, Analysis columns: Asahipak GF-310HQ, Asahipak GF-510HQ, Eluate: 20 mmol/L dimethyl formamide containing lithium bromide, Flow velocity: 0.6 mL/min) was used, and the calculation was performed from a calibration curve obtained using EasiVial (Registered Trademark) PEG/PEO (manufactured by Agilent Technologies).

Example 1

Synthesis of CYP-2PEG-1K×2

To 9.8 mg of a compound (C5cypate, hereinafter abbreviated as CYP) synthesized with reference to Bioconjugate Chem. 2005, 16, pp. 51 to 61, 58 mg of PG1-AM-1k (refer to Formula (p1) above) (manufactured by Nanocs, Mw 1000), 38 mg of 1-ethyl-3-[3-(dimethylamino)propyl]carbodiimide ((manufactured by Sigma-Aldrich, WSC), 16 mg of 1-hydroxybenzotriazole (manufactured by Dojindo Molecular Technologies, Inc., HOBt), 1 mL of anhydrous dimethyl formamide (manufactured by Wako Pure Chemical Industries, Ltd., dry DMF), and 5 mL of chloroform (manufactured by Kishida Chemical Co., Ltd., CHCl₃) were added, and then the mixture was stirred for 2.5 days under room temperature and under a light-blocked condition. The reaction solution was distilled off under reduced pressure and condensed, and then the resultant solution was dissolved again with 50 mL of chloroform. The solution was subjected to liquid separation using 50 mL of aqueous saturated ammonium chloride solution and then 50 mL of saturated salt solution. Anhydrous sodium sulfate (manufactured by Kishida Chemical Co., Ltd.) was added to the collected chloroform solution, and then the solution was filtered. The filtrate was distilled off under reduced pressure, and then isolation and purification were performed by silica gel column chromatography (Filler: Silica gel manufactured by Kishida Chemical Co., Ltd., 60 to 220 µm, 70 to 230 mesh, Mobile phase: Methanol (manufactured by Kishida Chemical Co., Ltd.)/Chloroform/Triethylamine (manufactured by Kishida Chemical Co., Ltd.)=1/5/0.06), whereby 11 mg of a green solid was obtained. FIG. 1 illustrates the reaction process of this example.

The absorption maximum in DMSO (manufactured by Wako Pure Chemical Industries, Ltd.) of the obtained compound was 794 nm. The mass spectrum had a distribution around a molecular weight of about 3000.

The measurement results of the ¹H-NMR spectrum of the compound obtained by the above-described synthesis are shown below: ¹H-NMR(CD₃OD/CDCl₃=1/1) (ppm): 8.14 (d), 7.97-7.92 (m), 7.62 (m), 7.53-7.44 (m), 6.56 (t), 6.20 (d), 4.13 (t), 3.76-3.47 (br), 3.34 (s), 2.23 (t), 1.98 (s), 1.88 (m), 1.72 (m), 1.52 (m).

In the following examples, reaction reagents, salts, and solvents manufactured by the same manufacturers as those described above were used Example 2

Synthesis of CYP-2PEG-0.55K×2

CYP-2PEG-0.55K×2 of Formula (I-1) was synthesized using PG1-AM-550 (refer to Formula (p1)) above) in the same manner as in Example 1. Reaction was performed for 3 days under room temperature and under a light-blocked condition, and then isolation and purification were performed by silica gel column chromatography (Mobile phase: Gradient of Methanol/Chloroform=1/20 to 1/5), Size exclusion column chromatography (Carrier: manufactured by GE Healthcare, Sephadex (Registered Trademark) LH-20, Mobile phase: Chloroform), whereby a green solid was obtained. The absorption maximum in DMSO was 794 nm. The mass spectrum had a distribution around a molecular weight of about 1900 as expected.

Example 3

Synthesis of CYP-2PEG-2K×2

CYP-2PEG-2k×2 of Formula (I-1) was synthesized using PG1-AM-2k (refer to Formula (p1)) above) in the same manner as in Example 1. Reaction was performed for 5 days under room temperature and under a light-blocked condition, and then isolation and purification were performed by ultrafiltration (Molecular weight cutoff: 5000, Solvent: 15 mM phosphate buffered saline), whereby a green solid was obtained. The absorption maximum in DMSO was 794 nm.

The mass spectrum had a distribution around a molecular weight of about 4200 as expected.

Example 4

Synthesis of CYP-2PEG-5K×2

CYP-2PEG-5K×2 of Formula (I-1) was synthesized using PG1-AM-5k (refer to Formula (p1) above) in the same manner as in Example 1. Reaction was performed under room temperature and under a light-blocked condition for 1 day at 45° C. for 4 hours, and then isolation and purification were performed by preparative layer chromatography (Mobile phase: Methanol/Chloroform/Diisopropylethylamine=1/20/0.02), whereby a green solid was obtained. The absorption maximum in DMSO was 794 nm. The mass spectrum had a distribution around a molecular weight of about 10600 as expected.

Example 5

Synthesis of CYP-2PEG-10K×2

CYP-2PEG-10K×2 of Formula (I-1) was synthesized using PG1-AM-10k (refer to Formula (p1) above) in the same manner as in Example 1. Reaction was performed under room temperature and under a light-blocked condition for 5 days, and then isolation and purification were performed by silica gel column chromatography (Mobile phase: Gradient of Methanol/Chloroform/Diisopropylethylamine (manufactured by Kishida Chemical Co., Ltd. company)=1/25/0.2 to 1/15/0.2) and ultrafiltration (Molecular weight cutoff: 10,000, Solvent: 15 mM phosphate buffered saline), whereby a green solid was obtained. The absorption maximum in DMSO was 794 nm. The mass spectrum had a distribution around a molecular weight of about 21700 as expected.

Example 6

Synthesis of C2CYP-2PEG-1 K×2

C2CYP-2PEG-1K×2 of Formula (I-2) was synthesized using a compound (cypate, hereinafter abbreviated as C2CYP) synthesized with reference to Bioconjugate Chem. 2005, 16, pp. 51-61 and PG1-AM-1k (refer to Formula (p1) above) in the same manner as in Example 1. Reaction was performed under room temperature and under a light-blocked condition for 5 days, and then purification was performed by a reprecipitation method (Methanol/Chloroform/Diethylether), whereby a green solid was obtained. The absorption maximum in DMSO was 794 nm. The mass spectrum had a distribution around a molecular weight of about 2700 as expected.

Comparative Example 1

Synthesis of CYP-2PEG-0.35K×2

CYP-2PEG-0.35K×2 of Formula (I-1) was synthesized using PG1-AM-350 (refer to Formula (p1) above) in the same manner as in Example 1. Reaction was performed for 3 days under room temperature and under a light-blocked condition, and then isolation and purification were performed by silica gel column chromatography (Mobile phase: Gradient of Methanol/Chloroform=1/15 to 1/5), whereby a green solid was obtained. The absorption maximum in DMSO was 794 nm. The mass spectrum had a distribution around a molecular weight of about 1500 as expected.

Comparative Example 2

Synthesis of CYP-2PEG-20K×2

A compound (CYP-2PEG-20K×2) represented by Formula (I-1) was synthesized using PG1-AM-20k (refer to Formula (p1) above) in the same manner as in Example 1. Reaction was performed under room temperature and under a light-blocked condition for 5 days, and then isolation and purification were performed by ultrafiltration (Molecular weight cutoff: 30000, Solvent: 15 mM phosphate buffered saline), whereby a green solid was obtained. The absorption maximum in DMSO was 794 nm. The peak showing an average molecular weight of 45000 was observed as expected by gel permeation chromatograph analysis.

Comparative Example 3

Synthesis of cy7-2PEG-1K×2 cy7-2PEG-1K×2 of Formula (C2) above was synthesized using Cyanine 7 bisacid (manufactured by AAT Bioquest, Inc.) and PG1-AM-1k (manufactured by Nanocs Inc., Mw 1,000) in the same manner as in Example 1. Reaction was performed for 1 day under room temperature and under a light-blocked condition, and then purification was performed by silica gel column chromatography (Mobile phase: Gradient of Methanol/Chloroform=1/5 to 3/4) and a dialysis method (Molecular weight cutoff: 1,000, Solvent: Methanol), whereby a green solid was obtained. The absorption maximum in the phosphate buffered saline was 750 nm. The mass spectrum had a distribution around a molecular weight of about 3000 as expected.

Comparative Example 4

Synthesis of cy7-2PEG-20K×2 cy7-2PEG-20K×2 of Formula (C2) above was synthesized using PG1-AM-20k (refer to Formula (p1) above) in the same manner as in Comparative Example 3. Reaction was performed under room temperature and under a light-blocked condition for 3 days, and then isolation and purification were performed by gel osmosis chromatography (Mobile phase: Methanol/Chloroform=1/1), whereby a green solid was obtained. The absorption maximum in phosphate buffered saline was 750 nm. The mass spectrum had a distribution around a molecular weight of about 43000 as expected.

Comparative Example 5

Synthesis of cy5-2PEG-1K×2

To 2.2 mg of Cyanine 5 bissuccinimidyl ester (manufactured by AAT Bioquest, Inc), 13 mg of PG1-AM-1k (refer to Formula (p1) above), 7 mg of 1-ethyl-3-[3-(dimethylamino)propyl]carbodiimide (WSC), 5 mg of 1-hydroxybenzotriazole (HOBt), 0.4 mL of anhydrous dimethylsulfoxide (dry DMSO), and 1 mL of chloroform ($CHCl_3$) were added, and then the mixture was stirred for 1 day under room temperature and under a light-blocked condition. The resultant mixture was purified by silica gel column chromatography (Mobile phase: Gradient of Methanol/Chloroform=1/5 to 3/4) and then a dialysis method (Molecular weight cutoff: 1000, Solvent: Methanol), whereby a blue solid was obtained. The absorption maximum in phosphate buffered saline was 650 nm. The mass spectrum had a distribution around a molecular weight of about 2900 as expected.

Comparative Example 6

Synthesis of cy5-2PEG-20K×2 cy5-2PEG-20K×2 shown in Formula (C3) was synthesized using PG1-AM-20k (refer to Formula (p1) above) in the same manner as in Comparative Example 5, Reaction was performed under room temperature and under a light-blocked condition for 4 days, and then isolation and purification were performed by gel osmosis chromatography (Mobile phase: Methanol/Chloroform=1/1), whereby a blue solid was obtained. The absorption maximum in phosphate buffered saline was 650 nm. The mass spectrum had a distribution around a molecular weight of about 43000 as expected.

Comparative Example 7

Synthesis of C10CYP-2PEG-0.35K×2

C10CYP-2PEG-0.35K×2 of Formula (C1) above was synthesized using a compound (C10cypate, hereinafter abbreviated as C10CYP) synthesized with reference to Bioconjugate Chem. 2005, 16, pp. 51-61 and PG1-AM-0.35k (refer to Formula (p1) above) in the same manner as in Example 1. Reaction was performed under room temperature and under a light-blocked condition for 5 days, and then purification was performed by a reprecipitation method (Methanol/Chloroform/Diethylether), whereby a green solid was obtained. The absorption maximum in DMSO was 794 nm. The mass spectrum had a distribution around a molecular weight of about 1580 as expected.

Evaluation of Accumulation Properties in Tumor

In order to confirm the accumulation properties in tumor of the compounds prepared in Examples and Comparative Examples, CYP-2PEG-20K×2, CYP-2PEG-1K×2, cy7-2PEG-20K×2, cy7-2PEG-1K×2, cy5-2PEG-20K×2, and cy5-2PEG-1K×2 were given to the tail vein of tumor-transplanted mice to which a colon-26 cell strain was transplanted. The given amount was set to 13 nmol in terms of the pigment amount. 24 hours after giving the same, blood was collected from the tail of the mice, the mice were euthanized with carbon dioxide, and then the colon-26 tumor tissue was extracted. The tumor tissue was moved to a plastic tube, a 1% Triton X-100 aqueous solution which was 1.25 times the weight of the tumor tissue was added thereto, and then the resultant tumor tissue was homogenated using a plastic pestle. Subsequently, the homogenate solution was subjected to a centrifugal operation (16000×G, for 5 minutes, at 4° C.) to collect a supernatant, and then dimethylsulfoxide (DMSO) (18 µL) was added to the supernatant (2 µL). With respect to the blood, a 1% Triton X-100 aqueous solution (11 µL) and DMSO (9 µL) were added to the collected blood (4 µL). By measuring the fluorescence intensity of the homogenate solution and the blood on a 48-well plate using ODYSSEY (Registered Trademark) CLx Infrared Imaging System (manufactured by LI-COR), the compounds according to Examples and Comparative Examples in the tumor tissue and the blood were quantified. The pigment transfer rate (% injected dose: abbreviated as % ID) to the tumor tissue based on the given amount (Pigment 13 nmol) per unit weight of the tumor tissue was shown as the accumulation amount in tumor of each compound (% ID/g) in Table 1. In this specification, the accumulation amount in the tumor tissue of the compound determined as described above is defined as 'I' (% ID/g) and the retention amount of the pigment in the blood of the compound is defined as B (% ID/g), and then a value obtained by dividing the T value by 13 is defined as an index of T/B (Accumulation amount in tumor/Retention amount in blood). The T/B of each of the compounds according to Examples and Comparative Examples was shown in Table 1. Similarly, CYP-2PEG-10K×2, CYP-2PEG-5K×2, CYP-2PEG-2K×2, CYP-2PEG-0.55K×2, CYP-2PEG-0.35K×2, C2CYP-2PEG-1K×2, and C10CYP-2PEG-0.35K×2 were given to the tail vain of tumor-transplanted mice to which a colon-26 cell strain was transplanted. 24 hours after giving the same, the T/B was measured. The results are shown in Table 1.

TABLE 1

| Sample name | | Molecular weight of one PEG | Accumulation amount in tumor (% ID/g) | T/B |
| --- | --- | --- | --- | --- |
| Ex. 1 | CYP-2PEG-1kx2 | 1k | 5.4 | 8.2 |
| Ex. 2 | CYP-2PEG-0.55kx2 | 0.55k | 0.3 | 2.1 |
| Ex. 3 | CYP-2PEG-2kx2 | 2k | 1.9 | 28.7 |
| Ex. 4 | CYP-2PEG-5kx2 | 5k | 3.6 | 2.2 |
| Ex. 5 | CYP-2PEG-10kx2 | 10k | 10.3 | 2.5 |
| Ex. 6 | C2CYP-2PEG-1kx2 | 1k | 1.4 | 2.1 |
| Comp. Ex. 1 | CYP-2PEG-0.35kx2 | 0.35k | — | 0.8 |
| Comp. Ex. 2 | CYP-2PEG-20kx2 | 20k | 9.7 | 0.4 |
| Comp. Ex. 3 | cy7-2PEG-1kx2 | 1k | 0.2 | — |
| Comp. Ex. 4 | cy7-2PEG-20kx2 | 20k | 13.6 | 0.7 |
| Comp. Ex. 5 | cy5-2PEG-1kx2 | 1k | 0.3 | — |
| Comp. Ex. 6 | cy5-2PEG-20kx2 | 20k | 19.9 | 1.2 |
| Comp. Ex. 7 | C10CYP-2PEG-0.35kx2 | 0.35k | 0.2 | 0.2 |

Conclusion

The results shown in Table I show that CYP-2PEG-1K×2 containing CYP which is a pigment having high hydrophobicity exhibits a high T/B ratio. This is considered to be because the apparent molecular weight increases due to hydrophobic association between molecules through the pigment and the renal excretion is suppressed as compared with the case of the pigment alone but the renal excretion is more rapidly performed than in the case of CYP-2PEG-20K×2, for example. Moreover, it was shown that the T/B ratio increases by reducing the molecular weight of PEG only in the combination of CYP and PEG. The T/B ratio in the range where the molecular weight of one PEG was 0.55 k to 10 k was higher than the T/B ratio of CYP-2PEG-20K×2 in which two PEGs having a molecular weight of 20 k were bonded to each other. The T/B ratio was 2 or higher in the range where the molecular weight of one PEG was 0.55 k to 10 k.

Similarly to the case of the results above, it was shown that, by setting the molecular weight of PEG of CYP-2PEG in a suitable range, the T/B ratio increases.

The compound according to the present invention has the structure in which PEG having a smaller molecular weight than that of a former PEG and a pigment having higher hydrophobicity than that of a former pigment are bonded to each other, and therefore the compound can give a contrast agent having a high T/B and capable of imaging a tumor with high contrast.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-249439, filed Dec. 9, 2014 which is hereby incorporated by reference herein in its entirety.

The invention claimed is:
1. A compound represented by any one of Formulae (I) to (III) and having a molecular weight of 1600 or more and 40000 or less;

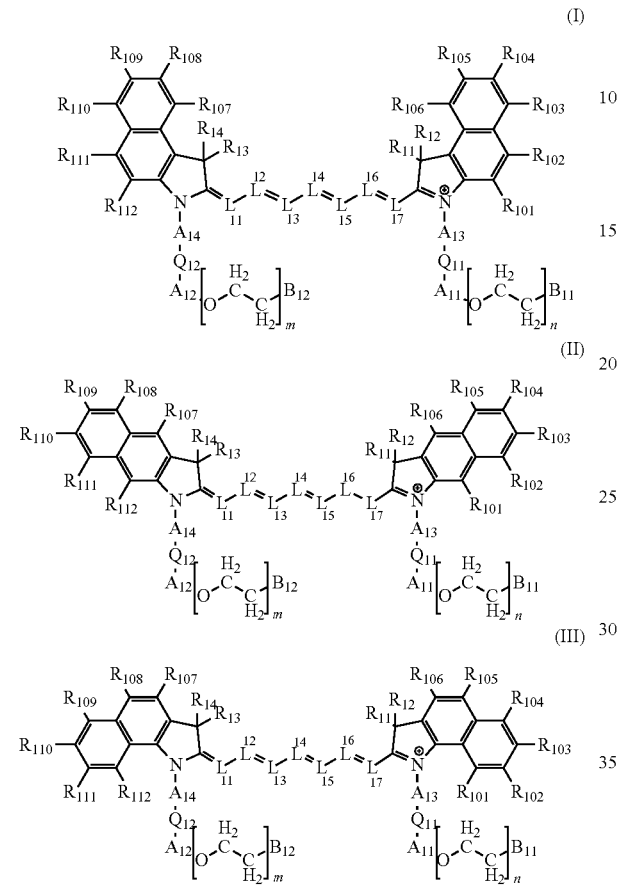

wherein in Formulae (I) to (III) above, n and m each independently represent an integer of 12 or more, $R_{101}$ to $R_{112}$ each independently represent any one of a hydrogen atom, a halogen atom, an acetoxy group, an alkyl group having 1 to 18 carbon atoms, an alkyl ester group having 1 to 18 carbon atoms, and an alkylamide group having 1 to 18 carbon atoms,
$R_{11}$ to $R_{14}$ each independently represent an alkyl group having 1 to 18 carbon atoms or a fluorinated alkyl group having 1 to 18 carbon atoms,
$L_{11}$ to $L_{17}$ each independently represent substituted or unsubstituted methine and a substituent of methine is an alkyl group having 1-4 carbon atoms or a halogen atom, $L_{11}$ and $L_{13}$, $L_{12}$ and $L_{14}$, $L_{13}$ and $L_{15}$, and $L_{14}$ and $L_{16}$ may form a five-membered ring or a six-membered ring, $A_{11}$ and $A_{12}$ represent alkylene groups having 1 to 3 carbon atoms, $A_{13}$ and $A_{14}$ represent alkylene groups having 2 to 5 carbon atoms, $Q_{11}$ and $Q_{12}$ represent —CONH—, and $B_{11}$ and $B_{12}$ represent;

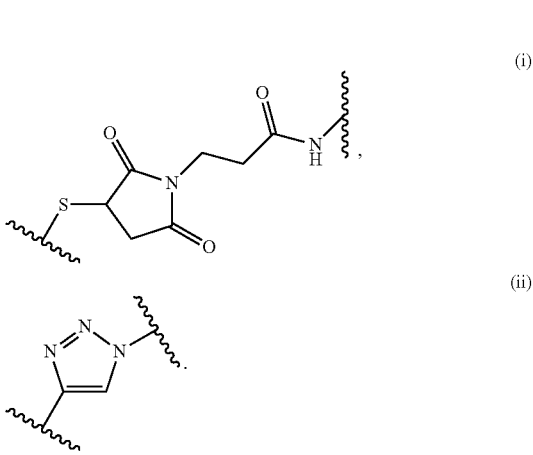

2. The compound according to claim 1, wherein a molecular weight of the compound is 2000 or more and 25000 or less.
3. The compound according to claim 1, wherein the molecular weight of the compound is 2500 or more and 11000 or less.
4. The compound according to claim 1, wherein the molecular weight of the compound is 2500 or more and 4500 or less.
5. The compound according to claim 1, wherein $R_{101}$ to $R_{112}$ in Formulae (I) to (III) above represent hydrogen atoms.
6. The compound according to claim 1, wherein $R_{11}$ to $R_{14}$ in Formulae (I) to (III) above represent methyl groups.
7. The compound according to claim 1, wherein $L_{11}$ to $L_{17}$ in Formulae (I) to (III) above represent unsubstituted methine.
8. A contrast agent for optical imaging, comprising:
the compound according to claim 1; and
a dispersion medium.
9. The compound according to claim 1, wherein the compound is a contrast agent for optical imaging.
10. The compound according to claim 1, wherein the compound is given into a living body and a ratio of an amount of the compound accumulated in tumor within the living body to an amount of the compound retained in blood within the living body of the compound is 1.5 or more.
11. The compound according to claim 1, wherein m and n each independently represent an integer of 22 or more to 45 or less.

* * * * *